United States Patent [19]

Dunn et al.

[11] Patent Number: 4,841,968
[45] Date of Patent: Jun. 27, 1989

[54] ANTITHROMBOTIC/THROMBOLYTIC SUTURE AND METHODS OF MAKING AND USING THE SAME

[75] Inventors: Richard L. Dunn, Birmingham, Ala.; John W. Gibson, Kingsport, Tenn.; Carlton A. Eddy; Leonard E. Laufe, both of San Antonio, Tex.

[73] Assignees: Southern Research Institute, Birmingham, Ala.; Texas Health Science Center, San Antonio, Tex.; a part interest

[21] Appl. No.: 912,400

[22] Filed: Sep. 26, 1986

[51] Int. Cl.$^4$ .............................................. A61L 17/00
[52] U.S. Cl. .................................... 128/335.5; 623/13; 424/78; 514/822; 128/334 R
[58] Field of Search ................... 128/335.5, DIG. 22, 128/334 R; 604/891, 892, 894; 623/1, 13, 66; 424/78; 514/822, 937, 941

[56] References Cited

U.S. PATENT DOCUMENTS

| | | | |
|---|---|---|---|
| 3,620,218 | 11/1971 | Schmitt et al. | 128/334 R |
| 3,791,983 | 2/1974 | Maierson | 252/305 |
| 3,845,761 | 11/1974 | Zaffaroni | 128/130 |
| 3,867,190 | 2/1975 | Schmitt et al. | 128/335.5 |
| 3,867,519 | 2/1975 | Michaels | 604/894 |
| 3,875,300 | 4/1975 | Homm et al. | 424/28 |
| 3,880,991 | 4/1975 | Yolles | 424/22 |
| 3,887,699 | 6/1975 | Yolles | 424/19 |
| 3,921,636 | 11/1975 | Zaffaroni | 604/892 |
| 3,926,188 | 12/1975 | Baker et al. | 128/260 |
| 3,991,766 | 11/1976 | Schmitt et al. | 128/335.5 |
| 4,118,470 | 10/1978 | Casey et al. | 424/19 |
| 4,122,129 | 10/1978 | Casey et al. | 128/335.5 |
| 4,136,252 | 1/1979 | Capozza et al. | 528/403 |
| 4,138,344 | 2/1979 | Choi et al. | 252/1 |
| 4,148,871 | 4/1979 | Pitt | 424/19 |
| 4,155,992 | 5/1979 | Schmitt | 424/19 |
| 4,280,954 | 7/1981 | Yannas et al. | 260/123.7 |
| 4,300,565 | 11/1981 | Rosensaft et al. | 128/335.5 |

OTHER PUBLICATIONS

Higgs et al., "Effect of Prostacylin (PGI$_2$) on Platelet Adhesion to Rabbit Arterial Subendothelium", Prostaglandins, vol. 16, No. 1, pp. 17–22.
Moncada et al, "Arachidonic Acid Metabolites and the Interactions Between Platelets and Blood Walts", N.E. Journal of Med., vol. 300, No. 20, pp. 1142–1147.
Smailis, et al., *Khirurgiya (Moscow)*, 53: 147–152.

Primary Examiner—Richard J. Apley
Assistant Examiner—Paul Prebilic
Attorney, Agent, or Firm—Needle & Rosenberg

[57] ABSTRACT

The controlled first-order release of either an antithrombotic or thrombolytic agent from a sutures at an anastomosis site is disclosed which prevents postoperative thrombosis and improves vascular patency in animals. A suitable polymer, such as polycaprolactone, is blended with prostacyclin or analogues of prostacyclin to form the suture material.

4 Claims, No Drawings

ANTITHROMBOTIC/THROMBOLYTIC SUTURE AND METHODS OF MAKING AND USING THE SAME

BACKGROUND OF THE INVENTION

The current technical ability to microsurgically anastomose blood vessels ranging in diameter from 0.5 to 2 mm has made possible a wide variety of microvascular surgical procedures including digital replantations, composite tissue grafts, and free flap transfers. Despite the almost routine nature with which small blood vessels are anastomosed, a significant failure rate continues to occur due to postoperative vascular occlusion. Establishing and maintaining vascular patency is particularly difficult with regard to anastomosis of small veins because of the increased technical difficulty, modest venous blood flow favoring postoperative thrombosis, and the tendency for prolonged venospasm to occur. [Hayhurst, J. W., and O'Brien, B. McC, An experimental study of microvascular technique, patency rates and related factors. Brit. J. Plast. Surg. 28:128, 1975]. Venous thrombosis after anastomosis is primarily caused by platelet aggregation and the formation of an occluding platelet thrombus leading to vascular stasis, simultaneous activation of the coagulation cascade, and the formation of a permanent fibrin clot. [Hardisty, R. M., Disorders of platelet function. Brit. Med. Bull. 33:207, 1977]. If the formation of the initial platelet thrombus could be decreased or prevented, patency rates would theoretically be improved.

Emerging knowledge concerning the maintenance of vascular homeostasis under normal, pathologic, and traumatically altered vascular conditions increasingly demonstrates a key role of endogenous prostacyclin, an effective vasodilator and the most potent inhibitor of platelet aggregation yet discovered. [Moncada, S., Gryglewski, R., Bunting, S., and Vane, J. R., An enzyme isolated from arteries transforms prostaglandin endoperoxides to an unstable substance that inhibits platelet aggregation. Nature 263:663, 1976; Ubatuba, F. B., Moncada, S., and Vane, J. R., The effect of prostacyclin ($PGI_2$) on platelet behavior. Thrombus formation in vivo and bleeding time. Thromb. Haemost. 41:425, 1979]. Prostacyclin, synthesized from precursors within the vessel wall by the endothelium, maintains vascular tone and protects the vessel wall against deposition of platelet aggregates. [Kaley, G., The role of prostaglandins in vascular homeostasis. Fed. Proc. 35:2358, 1976; Bourgain, R. H., Inhibition of $PGI_2$ (prostacyclin) synthesis in the arterial wall enhances the formation of white platelet thrombi in vivo. Haemostasis 7:252–255, 1978].

The enzyme necessary for prostacyclin synthesis is most abundant within the intima and progressively decreases in concentration toward the adventitia. In contrast, proaggregating activity, due primarily to collagen within the vessel wall, increases toward the adventitia. The blood vessel wall, therefore, exhibits a functional polarity, the endothelial lining being anti-aggregatory and the outer layers progressively more thrombogenic. [Moncada, S., and Amezcua, J. L., Prostacyclin, thromboxane $A_2$ interactions in haemostasis and thrombosis. Haemost. 8:252, 1979; Moncada, S., Herman, A. G., Higgs, E. A., and Vane, J. R., Differential formation of prostacyclin (PGX or $PGI_2$) by layers of the arterial wall. An explanation for the antithrombotic properties of vascular endothelium. Thromb. Res. 11:323, 1977].

Following vascular trauma and disruption of the endothelium, exposure of the underlying collagenous tissue leads to platelet activation and synthesis of thromboxane, a potent platelet aggregant and vasoconstrictor. The proaggregant activity of the collagenous vessel wall and platelet-derived thromboxane is normally balanced by the antagonistic effects of vessel wall-generated prostacyclin. The degree of vascular injury is therefore an important determinant of the ensuing vascular response. When vascular injury is slight, the normal equilibrium between prostacyclin and thromboxane is temporarily shifted toward thromboxane production leading to platelet aggregation and the formation of a transient hemostatic platelet plug sufficient to arrest hemorrhage but prevented, by endogenous prostacyclin, from enlarging intraluminally and causing vascular occlusion. When vascular trauma is severe, extensive exposure of platelets to collagenous vessel wall structures generates a major shift toward thromboxane synthesis and the simultaneous activation of the vascular coagulation cascade which may overwhelm the antagonistic effects of prostacyclin. The resulting wide-spread platelet aggregation, vasoconstriction, fibrin formation, and thrombosis leads to permanent vascular occlusion.

Because of its ability to inhibit platelet aggregation and induce vasodilation, prostacyclin is an attractive candidate as an antithrombotic agent. Used topically in an irrigant solution, prostacyclin has been shown to be effective in improving patency rates following arterial and venous microvascular anastomosis in the rat. [Leung, P. C., Chan, M. Y., and Roberts, M. B., The use of prostaglandins as local antithrombotic agents in microvascular surgery. Brit. J. Plast. Surg. 34:38, 1981; Emerson, D. J. M., Patel, C. B., Krishna, B. V., and Sykes, P. J., The use of prostacyclin in preventing occlusion of microvascular anastomoses by platelet thrombus: an experimental study in rats. Brit. J. Plast. Surg. 34:35, 1981]. However, topical application of prostacyclin to the adventitial surface of blood vessels requires its uptake by and penetration through the blood vessel wall in order to exert its effects.

SUMMARY OF THE INVENTION

It has been found that by incorporating an antithrombotic or thromboxane synthetase inhibiting agent or a thrombolytic or prostacyclin synthetase promoting agent (such as prostacyclin or its analogues) into sutures with controlled release characteristics, the particular agent is released intraluminally at the anastomosis site where it directly exerts its respective antithrombotic or thrombolytic effects. Numerous fibrous polymers suitable for use as suture material and as controlled delivery devices for the specific agents are available as excipients for the agents; the polymers are preferably biodegradable. Moreover, stable prostacyclin analogues with greater biological activity and a significantly longer biological half-life than the native compound are also available.

The fibrous delivery system of the present invention is prepared by the melt-spinning process for fiber fabrication because it is the most convenient and economical technique, although any convenient fabrication technique may be utilized. For instance, the fibers may be hollow having the agent and a suspending or dissolving composition, such as silicone oils and polyethylene glycol, in the center thereof. Also, the fibers may be constructed to have a core and sheath configuration with the core comprising a blend of the desired agent and polymer and the sheath comprising polymer, alone; the outer layer of polymer serves as a membrane to control the release of the agent from the fiber. Both of those fiber construction methods result in a zero order release of the agent. The experimental work was actually performed by blending prostacyclin analogues with polycaprolactone to form the sutures utilized in the transection and microvascular anastomosis of the common femoral vein in the rat, resulting in improved vascular patency rates.

DETAILED DESCRIPTION OF THE ILLUSTRATIVE EMBODIMENT

The following detailed description of the invention discloses prostacyclin or its analogues being incorporated into polycaprolactone and extruding the mixture into a fiber to which needles are attached for use as suture materials. However, it is understood that other agents can be incorporated into different excipients to form the sutures.

Examples of other antithrombotic/thrombolytic agents include Abbokinase (Abbott Laboratories, North Chicago, Ill.), Breokinase (Breon Laboratories, Inc., Park Ave. N.Y.), Coumadin, (Endo Laboratories, Inc., Garden City, N.J.), Dicumarol (Eli Lilly and Co., Indianapolis, Ind.), Dazoxiben (5-pyrazolyl, ethoxy benzoic acid), aspirin (acetylsalicylic acid), Indomethacin Indocin-Merck Sharpe & Sohme), Naproxen (Naprosyn-Syntex) and other acidic anti-inflammatory drugs such Ibuprofen. Other polymers which may be used include polyethylene, polypropylene, Nylon, polyethylene terephthalate, polyglycolide, poly(DL-lactide), poly(L-lactide), polydioxanone, polyhydroxybutyrate, polyorthoesters, polyesteramides, copolyoxalates, polycarbonate, polyanhydrides, poly(glutamic-co-leucine) and blends, copolymers and terpolymers thereof.

Preparation of Prostacyclin Sutures

The prostacyclin analogue Iloprost ® (Schering AG, Berlin) was selected for blending with polycaprolactone to form the suture used in the study. Polycaprolactone (PCL) (Union Carbide, Bound Brook, N.J.), a biocompatible, biodegradable aliphatic polyester, was used because of its low extrusion temperature (about 75° C.) compatible with the melting point of prostacyclin, its high prostacyclin solubility, and its mechanical strength, making it possible to load the polymer with high levels of drug and to obtain a fast release of the drug.

Prostacyclin was blended with the polymer at a loading of 2% Iloprost ® to 98% polycaprolactone by weight to produce a monolithic fiber with prostacyclin incorporated into the polymer matrix. The fused mixture was extruded and spun as a monofilament on a melt indexer and was drawn down to a diameter of 32-38 corresponding to a size of 9-0. The resultant suture nominally contained 0.25 micrograms of prostacyclin analogue per centimeter of suture. Polycaprolactone without prostacyclin analogue was similarly prepared to serve as a control. A comparison of the mechanical properties of prostacyclin-loaded sutures with commercial sutures shows that if the fibers are fully drawn, the elongation values and the strengths of the prostacyclin sutures are comparable to the commercial ones. All sutures were armed with a 100 micron ⅜ circle taper point needle (S & T 10 V 43).

A detailed description of the suture preparation is as follows:

Monolithic fibers were prepared containing 0.5, 2.0, and 5.0 Wt. % of prostacyclin analogues Iloprost ® and the sodium salt of that analogue, Iloprost ® Sodium. First, a uniform blend of the components was prepared by dissolving the PCL and prostacyclin compound in dichloromethane. A small quantity of ethanol was used to increase the solubility of one of the analogues. The blends were cast into films, and the films were cut into small strips and dried under vacuum at room temperature. The prostacyclin/PCL blends were melt spun into monolithic fibers with a Tinius Olsen Extrusion Plastometer. The chamber of the plastometer, with a spinneret inserted, was preheated to the desired spinning temperature. Then, the prostacyclin/PCL blend was loaded into the chamber. An extrusion ram was placed in the chamber, and a small weight was added to the ram to compress the blend. After the blend had equilibrated at the spinning temperature, additional weights were added to the ram to force the molten material through the spinneret. As the material extruded, it cooled and formed a fiber that was collected in loose coils. The fiber was immediately drawn by hand at room temperature to maximum elongation before breakage to reduce the diameter of the fiber to the size needed for sutures and to increase the mechanical strength of the fiber. Different ram weights and spinneret diameters were used to obtain monolithic fibers with reasonable properties and uniformity.

Five samples were cut from each fiber. The samples were tested on an Instron Tensile Tester according to standard ASTM procedures. The force required to break the fibers (load at break) and the percent of elongation of the fibers at break were recorded. The strength measurements were converted to tenacity values by dividing the load at break in grams by the fiber denier. Fiber denier is the weight in grams of 9000 meters of the fiber. Another value commonly used to compare the basic strengths of fiber is tensile factor. This value is derived from the product of the tenacity and square root of the elongation for a particular fiber.

The average tenacity value of the commercial sutures was 6 and the average tensile factor was 40, which were superior to the values obtained for the prostacyclin-loaded fibers. But the high values of elongation for the fibers compared to the relatively low values of elongation for the commercial sutures only indicated that the prostacyclin fibers had not been fully drawn.

Surgical Technique

Adult male Sprague-Dawley rats weighing 247 to 304 grams were used. Anesthesia was induced with intraperitoneal sodium pentobarbital (6 mg per 100 grams of body weight). Atropine sulphate (0.4 - 0.5 grams) was administered intraperitoneally to prevent respiratory distress. The femoral triangle was incised along the inguinal fold. Under visualization provided by a Zeiss OPMI 1 operating microscope, the common femoral vein, which measured 1.2 to 1.8 mm in diameter, was exposed from the inguinal ligament to the superficial epigastric vein and was separated from its associated artery and nerve by dissecting the surrounding perivascular sheath. Perforating venous branches were coagulated with bipolar microcautery forceps and were severed with microscissors. A rectangular sheet of black polyethylene film was loosely slipped beneath the fully mobilized vein to provide contrast during subsequent surgery. A small cotton swab moistened with 0.5 ml of 2% lidocaine was topically applied to relieve venospasm. Vessels were allowed to regain normal blood flow before surgery resumed. If venospasm failed to resolve, surgery on the vessel was terminated.

An 8 mm Acland approximating clamp with frame was applied and the vein was severed with microscissors. The cut ends were irrigated with Ringers lactate to remove blood. No attempt was made to excise adventitia or to mechanically dilate the cut ends of the vein. Using the technique described by Acland, an end-to-end anastomosis was performed using 8 or 9 interrupted sutures. [Acland, R. D., Microsurgery Practice Manual, C. V. Modsy, St. Louis, 1980.]Surgery was performed bilaterally. Prostacyclin containing sutures were used on one femoral vein and prostacyclin free control suture on the contralaterial vein. All surgery was performed by the same investigator without knowledge of the type of suture being use. The physical appearance and mechanical handling characteristics of prostacyclin containing and control sutures were identical thereby further precluding any bias by the surgeon. Only those anastomoses whose technical performance was without incident and was performed in comparable fashion were used in the study. Following release of the vascular clamps, hemostasis was confirmed and the skin incisions were closed without assessing vascular patency. No other anticoagulant therapy was given.

Femoral venous anastomosis was performed in fifteen rats. In thirteen, the procedure was completed bilaterally without technical difficulty and in two rats unilaterally. Of the resulting twenty-eight technically acceptable anastomoses, fifteen were performed using suture containing prostacyclin analogue and thirteen with control suture.

Patency Determination

Twenty-four hours after the anastomoses had been completed, each animal was again surgically anesthetized and each anastomosis was exposed and viewed through the operating microscope. The gross appearance was examined and each vein was gently freed of any surrounding connective tissue. Functional patency was assessed by clamping each vessel proximal to the anastomosis and severing the vein. Vigorous bleeding indicated patency. Animals were then killed with an overdose of anesthetic given intracardially and both anastomoses were surgically removed.

Morphologic Studies

The excised segment of vein containing the anastomosis was immediately immersed in 0.1M sodium cacodylate buffer (pH 7.4), cut open longitudinally, and pinned flat with the intimal surface exposed. Tissues were fixed overnight in a mixture of 4% gluteraldehyde and 1% paraformaldehyde in 0.1M cacodylate buffer.

Following fixation the tissue was dehydrated in graded concentrations of ethyl alcohol, placed in acetone, critical-point dried with $CO_2$, coated with gold palladium under vacuum, and examined in a JOEL JSM-35 scanning electron microscope (JOEL USA, Peabody, MA) at a power setting of 14KV.

In two additional animals the morphologic changes following anastomosis with prostacyclin-containing suture were examined five days and three weeks after surgery.

Patency rates were analyzed by Chi square analysis using Yate's correction.

Results

When examined twenty-four hours after surgery, all fifteen anastomoses performed using suture containing prostacyclin analogue were patent. Of the thirteen anastomoses performed with prostacyclin-free control suture, five were patent. This difference was highly significant ($P < 0.001$ $X^2 = 8.53$) (Table I).

TABLE I

PATENCY RATE FOLLOWING MICROVASCULAR END-TO-END ANASTOMOSIS OF THE COMMON FEMORAL VEIN IN THE RAT

| Treatment | No. of Veins | No. Patent | No. Occluded | Patency Rate |
|---|---|---|---|---|
| $PGI_2$-Analog | 15 | 15 | 0 | 100% |
| Control | 13 | 5 | 8 | 38% |

Functional Patency

All of the anastomoses performed using suture containing prostacyclin analogue exhibited a normal appearance consistent with vascular patency when viewed in the living, anesthetized subject. All fifteen veins were uniformly dilated proximal and distal to the anastomosis with no signs of constriction at the anastomosis site. All were filled with the venous blood of normal color. When clamped and transected proximal to the anastomosis, all fifteen vessels bled briskly and freely.

Among the thirteen veins anastomosed with prostacyclin-free control suture, five exhibited an appearance similar to that of the prostacyclin treated vessels and bled freely when transected proximally. The remaining eight were dilated distal to the anastomosis and were collapsed and largely empty of blood proximally. When transected, they failed to bleed.

Morphology

The surface morphology of those anastomoses performed with suture containing prostacyclin analogue was similar and exhibited an absence of thrombosis. Because of the large diameter suture used and the full thickness bites taken, the intimal surface was gathered into folds so that in no case was the anastomosis site smooth. There was minimal exposure of subintimal tissue. A light dusting of cellular debris, fibrin filaments, and neutrophils was present on the intimal surface in what appeared to be highly focal areas of early granulation formation. Similar findings were observed in the five patent control anastomoses.

The lumen in each of the eight veins that occluded following anastomosis with control suture exhibited a dense, well organized fibrinous clot. The clot filled the entire lumen and extended several millimeters from the anastomosis effectively sealing off the vessel.

In the two veins examined at five days and three weeks following anastomosis with suture containing prostacyclin analogue, both vessels were patent. At five days, intimal healing was nearly complete. Endothelial cells were seen extending over most of the anastomosis site with individual cells oriented parallel to the longitudinal axis of the vessel. Endothelium lined depressions were interspersed among raised areas, the latter corresponding to sites of suture placement. By three weeks, post anastomosis intimal healing was complete with a normal pattern of rugal folds extending across the anatomosis. Endothelium lined depressions and raised areas persisted along the anastomosis line.

Discussion

Prostacyclin analogue was highly effective in maintaining vascular patency following microsurgical venous anastomosis. The 100 percent patency rate achieved using suture containing prostacyclin analogue contrasted significantly with that obtained in prostacyclin-free control anastomoses, only a third of which were patent. Clearly, the vascular trauma associated with venous transection and anastomosis, despite the use of critical a priori criteria for accepting only those anastomoses which were accomplished without technical difficulty, was sufficient to cause thrombosis in the majority of controls. The high patency rate observed in those vessels repaired with suture containing prostacyclin analogue suggest that sufficient prostacyclin was released at the anastomosis site to effectively inhibit thrombosis and maintain patency. Unlike endogenous prostacyclin which has a biological half life in blood reported to range from thirty seconds to three minutes, the prostacyclin analogue used in the present study is biologically stable. [Moncada, S., and Vane, J. R., Arachidonic acid metabolites and the interactions between platelets and blood vessels. N. Engl. J. Med. 300:1142, 1979; Dusting, G., Moncada, S., and Vane, J. R., Disappearance of prostacyclin in the circulation of the dog. Br. J. Pharmacol. 62:414P, 1977]. Because the suture used is a monolithic fiber in which the prostacyclin analogue is homogeneously distributed, it exhibits a first order release rate. Preliminary studies indicate that approximately ten percent of the prostacyclin analogue is released in an initial burst in the first two hours followed thereafter by a slow sustained release of the remaining product over the next few days. Since thrombosis, if it occurs, takes place within the first hour following microvascular anastomosis, this pattern of initial rapid prostacyclin release would favor reversal of the acute effects of endothelial injury while the subsequent chronic slow release would modulate platelet-vessel wall interaction allowing the healing to occur. [Ubatuba, F. B., Moncada, S., and Vane, J. R., The effect of prostacyclin (PGI$_2$) on platelet behavior. Thrombus formation in vivo and bleeding time. Thromb. Haemost. 41:425, 1979; Acland, R. D., Prevention of thrombosis in microvascular surgery by the use of magnesium sulphate. Brit. J. Plast. Surg. 25:292, 1972]. It is understood, of course, that other antithrombotic/thrombolytic agents utilized in the present invention may evidence other controlled release rates.

A working hypothesis, therefore, is that prostacyclin analogue released from the suture inhibited platelet aggregation and thrombus formation without preventing the cooperative interaction of platelets with the exposed subendothelial vessel wall necessary for hemostasis and healing. [Marcus, A. J., Platelet function. N. Engl. J. Med. 289:1213, 1969; Honour, A. J., Pickering, G. A., and Sheppard, B. L., Ultrastructure and behavior of platelet thrombi in injured arteries. Brit. J. Exp. Pathol. 52:482, 1971; Johnson, S. A., In: The Circulating Platelet, (S. A. Johnson, ed.), Academic Press, New York, p. 283, 1971; Kitchens, C. S., and Weiss, L., Ultrastructural changes of endothelium associated with thrombocytopenia. Blood 46:567, 1975].

The amount of prostacyclin necessary to inhibit platelet aggregation and thrombus formation is much lower than that required to inhibit platelet adhesion to the subendothelial surface. As little as 0.1 ng of prostacyclin per milliliter of platelet-rich blood is capable of inhibiting thrombus formation in the de-endothelialized rabbit abdominal aorta while inhibition of platelet adhesion to the wall requires in excess of 20 ng/ml, an increase of two orders to magnitude. [Higgs, E. A., Moncada, S., Vane, J. R., Caen, J. R., Michel, H., and Tobelem, G., Effect of prostacyclin (PGI$_2$) on platelet adhesion to rabbit arterial subendothelium. Prostaglandins 16:17, 1978]. Although the release characteristics of prostacyclin analogue from the suture were not determined under the in vivo conditions of the present experiment, it would not be unreasonable, given the nominal content of 0.25 g/cm of suture, to assure that the amount of prostacyclin released into the vessel wall and lumen was sufficient to prevent thrombosis while allowing hemostasis and vessel repair to occur. The uniform spontaneous arrest of hemorrhage following completion of the anastomosis and release of the vascular clamps, the 100% patency rate, and the absence of thrombosis on the intimal surface twenty-four hours after anastomosis are all consistent with this hypothesis.

The effective amount of any particular antithrombotic/thrombolytic agent utilized in the fibrous delivery systems of the present invention depends, among other things, upon the size of the particular blood vessel involved in the surgery.

What we claim is:

1. A surgical suture material for preventing postoperative thrombosis at an anastomosis site in animals, comprising a blend of a polymer and an effective amount of an antithrombotic or thrombolytic agent whereby said agent has a first-order rate of release from said suture material at said site and wherein said agent is prostacyclin or an analogue of prostacyclin.

2. A surgical suture material for improving patency rates following arterial and venous microvascular anastomosis in animals, comprising extruded fibers of polycaprolactone and an effective amount of prostacyclin or an analogue of prostacyclin incorporated therein as a blend having first-order rate of release.

3. A method of improving patency after anastomosis in animals, comprising the step of performing the anastomosis with surgical suture material formed of fibers of a polymer having an effective amount of an antithrombotic or thrombolytic agent incorporated therein as a blend having a first-order rate of release, wherein said agent is prostacyclin or an analogue of prostacyclin.

4. A method of making surgical sutures, comprising the steps of:
   incorporating an effective amount of an antithrombotic or thrombolytic agent into a polymer to form a blend having first-order rate of release; and
   extruding said blend into a fibrous suture material, wherein said agent is prostacyclin or an analogue of prostacyclin.

* * * * *